(12) United States Patent
Ishihara et al.

(10) Patent No.: US 8,163,899 B2
(45) Date of Patent: Apr. 24, 2012

(54) PROCESS FOR PRODUCING LAUROLACTAM

(75) Inventors: Kazuaki Ishihara, Nagoya (JP); Junichi Kugimoto, Ube (JP); Joji Kawai, Ube (JP)

(73) Assignees: National University Corporation Nagoya University, Nagoya-shi (JP); UBE Industries, Ltd., Ube-shi (JP)

( * ) Notice: Subject to any disclaimer, the term of this patent is extended or adjusted under 35 U.S.C. 154(b) by 282 days.

(21) Appl. No.: 12/526,494

(22) PCT Filed: Feb. 8, 2008

(86) PCT No.: PCT/JP2008/052192
§ 371 (c)(1),
(2), (4) Date: Aug. 7, 2009

(87) PCT Pub. No.: WO2008/096873
PCT Pub. Date: Aug. 14, 2008

(65) Prior Publication Data
US 2010/0324283 A1 Dec. 23, 2010

(30) Foreign Application Priority Data
Feb. 9, 2007 (JP) .................................. 2007-030474

(51) Int. Cl.
*C07D 201/04* (2006.01)
(52) U.S. Cl. ........................................................ 540/464
(58) Field of Classification Search ................... 540/464
See application file for complete search history.

(56) References Cited

U.S. PATENT DOCUMENTS

| | | | |
|---|---|---|---|
| 3,410,832 A | 11/1968 | Griehl, et al. | |
| 3,431,255 A | 3/1969 | Strauss, et al. | |
| 3,437,655 A | 4/1969 | Garritsen, et al. | |
| 3,462,417 A | 8/1969 | Simmrock, et al. | |
| 6,649,757 B2 | 11/2003 | Kuroda et al. | |
| 2002/0058840 A1 | 5/2002 | Thiele et al. | |
| 2003/0065220 A1 | 4/2003 | Schiffer et al. | |
| 2003/0139596 A1 | 7/2003 | Kuroda et al. | |
| 2010/0029931 A1* | 2/2010 | Shibamoto et al. | 540/464 |

FOREIGN PATENT DOCUMENTS

| | | |
|---|---|---|
| EP | 487090 A | 5/1992 |
| EP | 2123635 A1 | 11/2009 |
| GB | 1148013 A | 4/1969 |
| JP | B-S43-012153 | 1/1964 |
| JP | B-S46-023740 | 7/1971 |
| JP | B-S47-018114 | 5/1972 |
| JP | B-S52-033118 | 8/1977 |
| JP | A-H05-004964 | 1/1993 |
| JP | H05-004964 A | 1/1993 |
| JP | A-H09-301951 | 11/1997 |
| JP | A-H09-301952 | 11/1997 |
| JP | A-2001-019670 | 1/2001 |
| JP | A-2001-072658 | 3/2001 |
| JP | A-2001-302602 | 10/2001 |
| JP | A-2001-302603 | 10/2001 |
| JP | A-2002-114746 | 4/2002 |
| JP | 2003-081930 A | 3/2003 |
| JP | A-2003-321453 | 11/2003 |
| JP | A-2004-099585 | 4/2004 |
| JP | A-2006-219470 | 8/2006 |
| WO | WO2007/105482 A1 | 9/2007 |
| WO | WO2007/125002 A1 | 11/2007 |
| WO | WO 2008/096873 A1 | 8/2008 |

OTHER PUBLICATIONS

Ishihara et al., Journal of American Chemical Society pp. 11240-11241 (2005).
International Search report issued in corresponding PCT Application No. PCT/JP2008/071044 mailed Feb. 24, 2009.
International Preliminary Report on Patentability and Written Opinion corresponding to PCT Application No. PCT/JP2008/071044, issued Jun. 8, 2010.
European Search report issued in corresponding European Patent Application No. EP 08711071, dated Oct. 7, 2010.
Furuya, Y. et al., Journal of American Chemical Society, pp. 11240-11241, 2005.
Narasaka, K. et al., Chemistry Letters, The Chemical Society of Japan, No. 3, pp. 489-492, 1993.
Sandhu, J.S. et al., Indian Journal of Chemistry, vol. 41B, pp. 154-156, 2002.
Yadav, J.S. et al., Journal of Chemical Research (S), pp. 236-238, 2002.
Zhu, M. et al., Tetrahedron Letters, pp. 4861-4863, 2006.
English translation of the International Preliminary Report on Patentability of PCT/JP2008/052192.

* cited by examiner

*Primary Examiner* — Bruck Kifle
(74) *Attorney, Agent, or Firm* — Knobbe Martens Olson & Bear LLP (57) ABSTRACT

Disclosed is a method for producing laurolactam from cyclododecanone and hydroxylamine in a simple process and with high efficiency. The method comprises the following steps (a) to (e): (a) reacting cyclododecanone with hydroxylamine in an aqueous solution in the presence of an excess amount of cyclododecanone or a solvent to produce cyclododecanone oxime; (b) separating the reaction mixture obtained after the oxime-forming step into an oil and an aqueous phases and collecting a solution of cyclododecanone oxime of the oil phase as; (c) removing dissolved water from the solution of cyclododecanone oxime which is collected as an oily phase in the oil/aqueous phase separation step; (d) producing laurolactam from cyclododecanone oxime by rearrangement reaction using an aromatic-ring containing compound as a rearrangement catalyst; and (e) separating the produced laurolactam from the reaction mixture after the rearrangement step and purifying the laurolactam.

9 Claims, 3 Drawing Sheets

PROCESS FOR PRODUCING LAUROLACTAM

CROSS-REFERENCE TO RELATED APPLICATIONS

This application is a U.S. National Phase of the International Application No. PCT/JP2008/052192 designating the U.S., filed Feb. 8, 2008 and published in Japanese on Aug. 14, 2008 as WO 2008/096873, which claims priority to Japanese Patent Application No. 2007-030474, filed Feb. 9, 2007.

TECHNICAL FIELD

The present invention relates to a process for producing laurolactam from cyclododecanone and hydroxylamine by an industrially convenient process.

BACKGROUND ART

A common industrial process for producing an amide compound involves Beckmann rearrangement of a corresponding oxime compound. For example, ε-caprolactam which is industrially useful is produced by Beckmann rearrangement of cyclohexanone oxime. Rearrangement catalysts used are generally concentrated sulfuric acid and oleum. Since these strong acids must be used in the stoichiometric amounts or more, they form a large amount of ammonium sulfate as a byproduct during neutralization. Although laurolactam, which is a starting material for Nylon 12, is also produced in a similar manner, the process is more complex because cyclododecanone oxime as an intermediate product has a high melting point. In producing ε-caprolactam, both cyclohexanone oxime and ε-caprolactam have a relatively lower melting point, so that oxime formation or rearrangement can be conducted in a solvent-free system, but production of laurolactam requires a reaction solvent. This reaction solvent must be able to substantially dissolve cyclododecanone oxime and be inert to concentrated sulfuric acid or oleum, and therefore the selection of the solvent is considerably restricted.

Only two processes are known for industrially producing laurolactam from cyclododecanone and an aqueous solution of hydroxylamine. One is a process commercially developed by Degussa Company. This method is as follows. Cyclododecanone is converted into an oxime using isopropylcyclohexane as a solvent, and after separating layers, a resulting solution of cyclododecanone oxime in isopropylcyclohexane is slowly added to concentrated sulfuric acid at a low temperature to prepare a solution of a cyclododecanone oxime sulfate adduct in sulfuric acid. After separating and recovering isopropylcyclohexane, the residual solution of cyclododecanone oxime sulfate adduct in sulfuric acid is heated to initiate Beckmann rearrangement of the oxime. After the rearrangement reaction, water is added to the system to dilute sulfuric acid, and then, the laurolactam produced is extracted with an organic solvent. Here, the extraction solvent may be isopropylcyclohexane or cyclododecanone. The extraction solvent is recovered by distillation from the resulting extraction solution and then laurolactam in the residue is purified by distillation (see, Patent Reference No. 1).

This process does not generate ammonium sulfate as a byproduct in the rearrangement reaction step, but requires enormously large facilities and energy for treating a large amount of waste diluted sulfuric acid. Furthermore, since cyclododecanone reacts with concentrated sulfuric acid to form a byproduct, the oxime-forming reaction must be completed for eliminating residual cyclododecanone, but due to hydrophobicity of isopropylcyclohexane, a mass transfer rate is low in an oil-water interface, leading to a longer oxime-forming reaction. As a whole, the process involves many steps of separation, recovery and recycling of solvents and, therefore, requires considerably large equipment expenses and energy.

Another industrial process is that commercially developed by Ube Industries-EMS. This process utilizes the fact that cyclohexanone oxime and caprolactam are good solvents for cyclododecanone oxime and laurolactam, respectively (for example, see Patent Reference 2). Specifically, a mixture of cyclododecanone and cyclohexanone is blended with an aqueous solution of hydroxylamine to produce oximes. Cyclohexanone oxime produced has a low melting point and is a good solvent for cyclododecanone oxime, so that the reaction can be conducted at 100° C. or lower and at an ambient pressure. Furthermore, cyclohexanone oxime is adequately hydrophilic for the oxime-forming reaction to quickly proceed, and the mixture is transferred to the rearrangement step without residual cyclohexanone or cyclododecanone. A rearrangement catalyst used is concentrated sulfuric acid or oleum. Whereas laurolactam produced has a high melting point, it is highly soluble in caprolactam having a low melting point. Therefore, the reaction can carried out even at a temperature of 100° C. or lower. The resulting rearrangement reaction solution is neutralized with ammonia water and then extracted with an organic solvent. Caprolactam can be dissolved in water to some extent, but is extracted into an organic solvent due to salting-out effect of ammonium sulfate. Next, a large amount of water is added to the solution containing extracted laurolactam and caprolactam, and caprolactam is extracted into the aqueous phase. From the separated organic phase, the organic solvent is recovered and laurolactam is purified by distillation. The aqueous phase is concentrated and after removing impurities, caprolactam is purified.

This process is excellent in that laurolactam and caprolactam can be produced together. However, as a process for producing laurolactam, has the following problems; (1) separation and purification of caprolactam requires large amounts of equipment expenses, resulting in low investment efficiency and the process involves operations of low energy efficiency such as concentration of an aqueous solution of caprolactam; (2) there is a restriction to a production ratio of laurolactam/caprolactam; and (3) caprolactam is a low-value-added product in comparison with laurolactam and an use efficiency of hydroxylamine is low.

Recently, there have been intensely investigated rearrangement catalysts which do not require a large amount of sulfuric acid or oleum. As a system containing a strong acid, there have been reported a mixture of rhenium peroxide ammonium salt and trifluoromethane sulfonic acid (Non-Patent Reference 1), indium triflate (Non-Patent Reference 2) and ytterbium triflate (Non-Patent Reference 3). Known methods utilizing a system containing an acid and a dehydrating agent include a method of conducting rearrangement reaction using phosphorous pentoxide or a condensed phosphoric acid compound and a fluorine-free sulfonic anhydride or sulfocarboxylic anhydride in a N,N-disubstituted amide compound as a solvent (Patent References 3 and 4) and a method using a zeolite catalyst pre-treated with an aqueous acid-containing solution (Patent Reference 5). As methods that use no acids, there have been suggested a method of conducting rearrangement reaction in the presence of a rhenium compound and a nitrogen-containing heterocyclic compound (Patent References 6 and 7) and a method of using zinc oxide (Patent Reference 8). Patent Reference 9 has disclosed a method of reacting an oxime and a carboxylic acid in a carboxylic acid solvent using cyanuric chloride (trichlorotriazine) as a dehydrating agent, whereby producing an ester which is then subjected to rearrangement reaction. Patent Reference 10 has disclosed a method where an oxime hydrochloride is subjected to rearrangement using cyanuric chloride (trichlorotriazine) as an initiator.

Although some of these catalysts and manufacturing processes can provide a high rearrangement yield, these methods employ special catalysts and/or solvents, for which a recovering or recycling procedure is not disclosed, and these are, therefore, unestablished as an industrial process.

Patent Reference 11 has described Beckmann rearrangement of an oxime compound in a polar solvent, wherein a rearrangement catalyst used is an aromatic compound (1) containing, as aromatic-ring member, at least one carbon atom having a leaving group, (2) containing at least three aromatic-ring members which are either or both of heteroatoms or/and carbon atoms having an electron-withdrawing group, and (3) wherein, two of the heteroatoms and/or carbon atoms having an electron-withdrawing group are at the ortho- or para-position to the carbon atom having an electron-withdrawing group. A similar description can be found in Non-Patent Reference 4. Non-Patent Reference 5 discloses that a phosphoric acid salt having a heterocyclic structure similar to that in Patent Reference 11 is active for Beckmann rearrangement.

The catalyst disclosed in Patent Reference No. 11 is highly active for a rearrangement reaction of cyclododecanone oxime to provide laurolactam in a high yield, and is, therefore, suitable as a rearrangement reaction catalyst in producing laurolactam. However, a nitrile which is recommended as a solvent cannot be used for an oxime-forming reaction because it reacts with hydroxylamine to form an amidoxime. Furthermore, since it is susceptible to hydrolysis, the loss of the catalyst inevitably happens in the step of removing catalyst and the like. Since it is highly miscible with water, a process for dehydrating materials for rearrangement becomes complex. Therefore, for establishing a practically feasible industrial process, solvents and processes must be selected, in consideration of individual steps from starting materials to a final product including an oxime-forming step.

Patent Reference 1: Japanese examined patent publication No. S52-033118 (1977-033118).

Patent Reference 2: Japanese Laid-open patent publication No. H05-4964 (1993-4964).

Patent Reference 3: Japanese Laid-open patent publication No. 2001-302602.

Patent Reference 4: Japanese Laid-open patent publication No. 2001-302603.

Patent Reference 5: Japanese Laid-open patent publication No. 2001-072658.

Patent Reference 6: Japanese Laid-open patent publication No. H09-301951 (1997-301951).

Patent Reference 7: Japanese Laid-open patent publication No. H09-301952 (1997-301952).

Patent Reference 8: Japanese Laid-open patent publication No. 2001-019670.

Patent Reference 9: Japanese examined patent publication No. S46.23740 (1971-23740).

Patent Reference No. 10: Japanese examined patent publication No. S47-18114 (1972-18114).

Patent Reference No. 11: Japanese Laid-open patent publication No. 2006-219470.

Non-Patent Reference 1: K. Narasaka, et. al., Chemistry Letter, pp. 489-492 (1993).

Non-Patent Reference 2: J. S. Sandhu, et. al., Indian Journal of Chemistry, pp. 154-156 (2002).

Non-Patent Reference 3: J. S. Yadav, et. al., Journal of Chemical Research(S), pp. 236-238 (2002).

Non-Patent Reference 4: K. Ishihara, et. al., Journal of American Chemical Sociaty, pp. 11240-11241 (2005).

Non-Patent Reference 5: M. Zhu, et. al., Tetrahedron Letters, pp. 4861-4863 (2006).

DISCLOSURE OF THE INVENTION

Subject to be Solved by the Invention

An objective of the present invention is to provide a process for efficiently producing laurolactam from cyclododecanone and hydroxylamine by a convenient process. Another objective of the present invention is to provide a process for producing laurolactam using a combination of inexpensive facilities.

Means to Solve the Subject

The present invention relates to the following items.

[1] A process for producing laurolactam comprising the steps of:

(a) reacting cyclododecanone with hydroxylamine in an aqueous solution in the presence of an excess amount of cyclododecanone or a solvent to produce cyclododecanone oxime (hereinafter, referred to as an "oxime-forming step");

(b) separating the reaction mixture obtained after said oxime-forming step into an oil and an aqueous phases and collecting a solution of cyclododecanone oxime of the oil phase (hereinafter, referred to as an "oil/aqueous phase separation step");

(c) removing dissolved water from said solution of cyclododecanone oxime which is collected as an oil phase in said oil/aqueous phase separation step (hereinafter, referred to as a "dehydration step";

(d) producing laurolactam from cyclododecanone oxime by rearrangement reaction using an aromatic-ring containing compound as a rearrangement catalyst (hereinafter, referred to as a "rearrangement step"; and (e) separating the produced laurolactam from the reaction mixture after said rearrangement step and purifying the laurolactam (hereinafter, referred to as a "separation/purification step").

[2] The process for producing laurolactam as described in [1], wherein the aromatic ring in said aromatic-ring containing compound has a structure (1) comprising at least one carbon atom having a leaving group as a ring member of the aromatic ring and (2) comprising at least two carbon atoms having an electron-withdrawing group as ring members of the aromatic ring, and (3) wherein, three of the nitrogen atoms and/or the carbon atoms having an electron-withdrawing group, each of which is a ring member of the aromatic ring are at the ortho and the para positions to the carbon atom having a leaving group described in (1).

[3] The process for producing laurolactam as described in [2], wherein said aromatic ring is benzene, pyridine, pyrimidine or triazine and comprises a halogen atom as said leaving group.

[4] The process for producing laurolactam as described in [2], wherein said aromatic-ring containing compound is selected from the group consisting of 4-chloro-3,5-dinitrobenzonitrile, picryl chloride, 2-chloro-3,5-dinitropyridine and trichlorotriazine.

[5] The process for producing laurolactam as described in any one of [1] to [4], wherein in said dehydration step, a content of residual water in the cyclododecanone oxime solution is reduced to 1000 ppm or less.

[6] The process for producing laurolactam as described in [5], wherein in said dehydration step, a content of residual water in the cyclododecanone oxime solution is reduced to 100 ppm or less.

[7] The process for producing laurolactam as described in any one of [1] to [6], wherein in said oxime-forming step, the reaction is conducted in the presence of a solvent selected from carboxylic acid esters and tertiary alcohols.

[8] The process for producing laurolactam as described in any one of [1] to [6], wherein in said oxime-forming step, the reaction is conducted in the presence of an excessive amount of cyclododecanone and in said separation/purification step, cyclododecanone is recovered and at least partially recycled to said oxime-forming step.

[9] The process for producing laurolactam as described in any one of [1] to [8], wherein in said separation/purification step, water is added to the reaction mixture after the rearrangement step to convert said aromatic-ring containing compound of the rearrangement catalyst into a water-soluble compound and the aqueous layer is separated from the solution containing laurolactam.

[10] The process for producing laurolactam as described in any one of [1] to [8], wherein in said separation/purification step, said rearrangement catalyst is recovered from the reaction mixture after the rearrangement step and recycled to said rearrangement step.

[11] The process for producing laurolactam as described in [10], wherein in said separation/purification step, laurolactam is isolated by crystallization from the reaction mixture after the rearrangement step, and said rearrangement catalyst is recovered in the crystallization mother liquid and recycled to said rearrangement step.

[12] The process for producing laurolactam as described in [10] or [11], wherein in said rearrangement step, the conversion of cyclododecanone oxime is 95% or less.

Effect of the Invention

Since the present invention does not employ concentrated sulfuric acid or oleum, byproducts such as ammonium sulfate are not produced, and the required steps such as neutralization, extraction/separation and distillation/collection are significantly reduced in comparison with a conventional method and therefore a convenient process for producing laurolactam is realized.

Furthermore, since the oxime-forming reaction and the rearrangement reaction are conducted in the same solvent, a production process is simplified and the solvent can be easily recycled.

BEST MODE FOR CARRYING OUT THE INVENTION

The present invention will be described in detail.

In the process for producing laurolactam, selection of a rearrangement catalyst is important. A rearrangement catalyst suitably used in the present invention is an aromatic-ring containing compound. An aromatic-ring containing compound used as a rearrangement catalyst is preferably an organic compound having a structure (1) containing at least one carbon atom having a leaving group as a ring member of the aromatic ring and (2) containing at least two carbon atoms having an electron-withdrawing group as ring members of the aromatic ring, and (3) wherein, three of the nitrogen atoms and/or the carbon atoms having an electron-withdrawing group, each of which is a ring member of the aromatic ring, are at the ortho and the para positions to the carbon atom having a leaving group described in (1).

Preferable examples of the aromatic ring include monocyclic or polycyclic aromatic rings such as benzene, biphenyl, terphenyl and triphenyl; fused polycyclic aromatic rings such as naphthalene, anthracene, fluorene, phenanthrene, azulene and pyrene; and aromatic heterocycles such as pyrrole, furan, thiophene, imidazole, pyrazole, triazole, tetrazole, oxazole, isoxazole, thiazole, isothiazole, furazanpyridine, pyrazine, pyrimidine, pyridazine and triazine; particularly preferably, benzene, pyridine, pyrimidine and triazine.

Examples of a leaving group may include halogen (fluorine, chlorine, bromine and iodine), sulfonyloxy {aryl sulfonyloxy such as benzenesulfonyloxy and p-toluenesulfonyloxy (tosyl) OTs; and alkanesulfonyloxy such as methanesulfonyloxy OMs, trifluoromethanesulfonyloxy (triflate) OTf, trichloromethanesulfonyloxy and ethanesulfonyloxy and the like}, sulfonyl halide (sulfonyl chloride, sulfonyl bromide and the like), diazonium, and carbonyl halide (carbonyl chloride). Particularly preferred is halogen, especially chlorine.

An electron-withdrawing group may be any known electron-withdrawing group without limitations and includes cyano, trifluoromethyl, trichloromethyl, nitro, halide (halogen), carbonyl and sulfonyl, preferably cyano and nitro.

Specific examples of a rearrangement catalyst may include benzene-ring compounds such as 4-chloro-3,5-dinitrobenzonitrile, 4-fluoro-3,5-dinitrobenzonitrile, 4-bromo-3,5-dinitrobenzonitrile, 4-chloro-1,3,5-trinitrobenzene, 4-trifluoromethyl-3,5-dinitrobenzonitrile, 4-p-toluene sulfonyloxy-3,5-dinitrobenzonitrile, picryl chloride, picryl bromide and picryl fluoride, and heterocyclic compounds such as 2-chloro-3,5-dinitropyridine, 2-bromo-3,5-dinitropyridine, 2-fluoro-3,5-dinitropyridine, trichlorotriazine, tribromotriazine and trifluorotriazine.

Particularly preferable examples include 4-chloro-3,5-dinitrobenzonitrile, picryl chloride, 2-chloro-3,5-dinitropyridine and trichlorotriazine, and particularly preferred is trichlorotriazine, which is highly active and inexpensive.

In the production process of the present invention, cyclododecanone and hydroxylamine are used as starting materials. Cyclododecanone can be readily available as an industrial agent. For example, Invista Company sells a mixture of cyclododecanone and cyclododecanol, and therefore, after cyclododecanol in the mixture is converted by dehydrogenation into cyclododecanone, the product can be used.

The other starting material, hydroxylamine, which is unstable, is produced and sold as an aqueous solution of a hydroxylamine salt such as hydroxylamine sulfate and hydroxylamine carbonate. Before the reaction, a base such as ammonia water is added to the solution to liberate hydroxylamine, which is to be used. An aqueous solution of hydroxylamine in which hydroxylamine has been already liberated may be fed to the oxime-forming step, but generally, an aqueous solution of a hydroxylamine salt (preferably, sulfate) and a base (preferably, ammonia water) are fed to an oxime-forming reactor to liberate hydroxylamine in the reactor.

Since cyclododecanone oxime produced has a high melting point, the oxime-forming reaction and the rearrangement reaction require a solvent capable of dissolving cyclododecanone oxime. Therefore, in the present invention, the cyclododecanone of a starting material may be fed in an excessive ratio to the amount of hydroxylamine so that the excessive cyclododecanone not involved in the reaction is used as a solvent. Alternatively, the reaction is conducted using a compound other than the starting material as a solvent.

Unless otherwise stated explicitly, the term "solvent" in the description below does not include cyclododecanone.

A solvent suitably used in the present invention must be not only preferable as a solvent for the oxime-forming reaction (hereinafter, referred to as an "solvent for oxime formation") but also as a solvent for the rearrangement reaction (hereinafter, referred to as a "solvent for rearrangement").

One of the requirements of a solvent for oxime formation is higher solubility for dissolving cyclododecanone oxime (i.e. solution-forming properties of the solvent). When a solubility parameter as defined by the following equation is used as an index, a solvent having the parameter of 7.5 to 13.0, particularly 8.0 to 12.5 exhibits high solubility for dissolving cyclododecanone oxime.

Here, a solubility parameter indicates strength of an intermolecular binding force such as hydrogen bond, and generally the higher parameter shows the higher polarity. Compounds having close solubility parameter values exhibits high compatibility. This parameter can be calculated from $\Delta H^V$, a standard boiling point and density data, and $\Delta H^V$ can be estimated from a molecular structure. Herein, some solvents were measured for a solubility of cyclododecanone oxime and compared it with a calculated solubility parameter to determine an index.

$$\delta = ((\Delta H^V - RT)/V)^{1/2}$$

wherein δ: solubility parameter, $\Delta H^V$: evaporation enthalpy change, R: gas constant, T: absolute temperature, V: molar volume.

Solvents which are reactive with cyclododecanone and/or hydroxylamine must be excluded even if they are good solvent exhibiting high dissolving power to cyclododecanone oxime. For example, ketones or aldehydes cannot be used because they react with hydroxylamine to form ketoximes or aldoximes, respectively. Nitrile react with hydroxylamine to form amidoximes. Amides also react with hydroxylamine to form adducts with the hydroxylamine. Furthermore, amines react with cyclododecanone to form Schiff bases. These solvents are excluded, even if they exhibit high solubility for dissolving cyclododecanone oxime.

Usable solvents for oxime formation are those that exhibit high solubility for dissolving cyclododecanone oxime and are inert to cyclododecanone and/or hydroxylamine; the examples thereof include alicyclic hydrocarbons, hydrogenated fused aromatic ring compounds, aromatic hydrocarbons, medium and higher alcohols, ethers, glymes and esters.

Among these, highly hydrophobic solvents leads to a slow oxime-formation rate and thus a longer reaction time. On the other hand, highly hydrophilic solvents are soluble in an aqueous phase and thus must be recovered from both oil and aqueous phases, which is disadvantageous in the aspects of facilities and energy. For example, due to the above reason, disadvantageous are chain hydrocarbons such as n-hexane, n-octane, isooctane, n-decane and n-dodecane, water-soluble alcohols and ethers having 1 to 2 carbon atoms such as methanol, ethanol and ethyleneglycol. In contrast, hydroxylamine is insoluble and an oxime-forming reaction rate is low in aromatic compounds such as benzene, toluene and xylene, hydrogenated fused aromatic ring compounds such as tetralin and decalin and alicyclic hydrocarbons having a side chain such as isopropylcyclohexane.

Therefore, medium and higher alcohols, ethers, glymes (polyethers obtained by condensation of ethylene glycol) and esters, which exhibit moderate hydrophilicity, may be particularly preferable as a solvent for oxime formation.

Requirements of a solvent for rearrangement are that (1) it has a higher solubility for dissolving cyclododecanone oxime and laurolactam, (2) it dissolve the above rearrangement catalyst without reacting with the rearrangement catalyst, and (3) it can be easily recovered and recycled and is thermally and chemically stable.

Alicyclic hydrocarbons, hydrogenated fused aromatic ring compounds, aromatic hydrocarbons, medium and higher alcohols, ethers, glymes and esters listed above as a solvent for oxime formation can be generally used as a solvent for rearrangement when they are less reactive to a rearrangement catalyst. Among medium and higher alcohols, ethers, glymes and esters which are preferable as a solvent for oxime formation, esters and tertiary alcohols are particularly preferable as described below.

Because they are moderately hydrophilic and inert to a rearrangement catalyst, esters are suitable solvents in both oxime-forming and rearrangement steps. Suitable esters are carboxylic acid esters and there are no restrictions in use as long as they have a melting point of 100° C. or less. Examples which can be used as a solvent include ethyl acrylate, butyl acrylate, methyl acrylate, dibutyl adipate, ethyl acetoacetate, methyl acetoacetate, ethyl isovalerate, methyl isovalerate, ethyl isobutyrate, methyl isobutyrate, diethyl itaconate, isobutyl formate, isopentyl formate, butyl formate, propyl formate, pentyl formate, ethyl valerate, diethyl glutarate, ethyl crotonate, diethyl succinate, isobutyl acetate, isopropyl acetate, ethyl acetate, butyl acetate, s-butyl acetate, t-butyl acetate, ethyl acetate, methyl acetate, pentyl acetate, hexyl acetate, benzyl acetate, ethyl nonanoate, diethyl phthalate, dibutyl phthalate, dimethyl phthalate, ethyl hexanoate, ethyl heptanoate, methyl methacrylate, ethyl butyrate, butyl butyrate and methyl butyrate, particularly preferably ethyl acetate and n-butyl acetate which are less viscous, inexpensive and readily available.

Medium and higher alcohols which are suitable as a solvent for oxime formation were believed to be generally inappropriate as a solvent for rearrangement. It is because an alcohol reacts with the above rearrangement catalyst to form an alkyl aryl ether. For example, 1-propanol reacts with trichlorotriazine to form propoxydichlorotriazine, which is finally converted into tripropoxytriazine. These alkyl aryl ethers are ineffective as a rearrangement catalyst.

We have, however, intensely investigated a rearrangement reaction of cyclododecanone oxime in the presence of an alcohol, and have discovered that a reaction between an alcohol and a catalyst is considerably slower than an aryl ether-formation reaction between cyclododecanone oxime and a catalyst. In particular, when a tertiary alcohol is used, an ether-formation reaction between a catalyst and an alcohol can be ignored if cyclododecanone oxime is present in the reaction system. In other words, the use of a tertiary alcohol as a solvent allows for conducting the oxime-forming reaction and the rearrangement reaction in the same solvent, resulting in a simple process for producing laurolactam. There are no particular restrictions to the type of a tertiary alcohol; and for example, aliphatic (including alicylic) alcohols having about 4 to 18, preferably 4 to 12, particularly preferably 4 to 8 carbon atoms may be used. Examples include t-butanol, t-amyl alcohol, 2-methyl-2-pentanol, 3-methyl-3-pentanol, 1-methylcyclopentanol and 1-methylcyclohexanol, and particularly preferred is t-butanol which is inexpensive and readily available.

Similar to the reaction of the above alcohols, ethers and glymes having a terminal hydroxy group react with a rearrangement catalyst to form an alkyl aryl ether which is inactive in the rearrangement reaction. Therefore, those do not have a hydroxyl group are generally preferable. An ether with a terminal capped with an alkyl group becomes hydrophobic, generally leading to a slower oxime-formation rate.

Production Steps

There will be described a process for producing laurolactam along the production steps. The following descriptions are, unless otherwise stated, applied to both of the cases using an excessive amount of cyclododecanone and using a solvent.

Oxime-Forming Step

In the oxime-forming step cyclododecanone is reacted with an aqueous solution of hydroxylamine to form cyclododecanone oxime. During the oxime-forming step, the reaction mixture is not homogeneous and an aqueous solution of hydroxylamine exsists as an aqueous phase while a cyclododecanone or cyclododecanone solution exsists as an oil phase. Cyclododecanone oxime produced as the reaction product is dissolved in the oil phase.

Although the oxime-forming reaction may be conducted at a high temperature, the reaction at a temperature of 100° C. or higher requires a pressurized vessel because hydroxylamine is used as an aqueous solution. The reaction is, therefore, preferably conducted at 100° C. or lower and under the ambient pressure. On the other hand, the reaction at a lower temperature leads to reduction in a reaction rate. A temperature is, therefore, preferably 60° C. or higher, more preferably 75° C. or higher. When cyclododecanone is used in an excessive amount, a temperature is preferably 80° C. or higher, particularly 90° C. or higher.

This reaction can be conducted in the open-air, but preferably in an atmosphere of an inert gas such as argon and helium.

A reaction time needed for the oxime-forming reaction varies depending on a temperature, and is 0.5 to 10 hours, preferably 1 to 6 hours when the reaction is conducted at 75° C. to 95° C. When a reaction time is too short, unreacted starting materials (i.e. hydroxylamine and cyclododecanone when a solvent is used; or hydroxylamine when an excessive amount of cyclododecanone is used) remain. The unreacted reactants may be recycled to, for example, the starting material preparation step, but it is not preferable because it requires a recycling facility. A too long reaction time is not preferable because an oxime-forming apparatus becomes larger.

An oxime-forming reactor may be a common reactor such as batch reactor, semi-batch reactor, tubular reactor and tank flow reactor, and particularly continuous stirred tank flow reactor (CSTR) are suitable. When CSTR is used, an aqueous solution of hydroxylamine is fed to a first reactor and a cyclododecanone solution (or cyclododecanone alone) is fed to the final reactor, and it is desirable that an aqueous phase is transferred to the latter reactor and an oil phase is transferred to the former reactor sequentially so that reactants are completely reacted without remaining unreacted reactants.

When the reaction is conducted using an excessive amount of cyclododecanone, the lower limit of a ratio of cyclododecanone to hydroxylamine fed to the oxime-forming step is defined by a solubility of cyclododecanone oxime in cyclododecanone. When cyclododecanone is used in an excessively small amount, precipitation of cyclododecanone oxime may produce in the steps from the oxime-forming step to the rearrangement step, leading to deterioration in handling properties. Since a solubility depends on a temperature, the ratio and a step temperature are determined within a range in which cyclododecanone oxime does not precipitate from the oxime-forming step to the rearrangement step. When the lowest temperature from the oxime-forming step to the rearrangement step is 95° C., 400 to 1400 parts by weight, preferably 600 to 900 parts by weight of cyclododecanone is used to 100 parts by weight of pure content of hydroxylamine. When the amount of cyclododecanone is too excessive, cyclododecanone oxime and laurolactam will be produced in a low concentration, requiring a very large reactor or cyclododecanone-recovering tower, which leads to deterioration in productivity.

When the above feeding rate of cyclododecanone is expressed by an excess percentage (the feeding amount of cyclododecanone/the amount of cyclododecanone to be reacted (%)), it corresponds to 172 to 353%, preferably 208 to 263%.

When a solvent is used, hydroxylamine and cyclododecanone are generally preferably fed in a substantially equimolar ratio. When the amount of a solvent is too small in terms of a feeding ratio of cyclododecanone to a solvent, cyclododecanone oxime may precipitate from the oxime-forming step to the rearrangement step, leading to deterioration in handling properties. Since a solubility depends on a solvent used and a temperature, the ratio and a step temperature are preferably determined within a range in which cyclododecanone oxime does not precipitate from the oxime-forming step to the rearrangement step. When the lowest temperature from the oxime-forming step to the rearrangement step is 75° C., 5 to 30 parts by weight, preferably 15 to 27 parts by weight of a solvent is used to 100 parts by weight of cyclododecanone. When the amount of a solvent is too excessive, cyclododecanone oxime and laurolactam will be produced in a low concentration, requiring a very large reactor or solvent-recovering tower, which leads to deterioration in productivity.

When cyclododecanone is used in an excessive amount, a surfactant or hydrophilic solvent may be, if necessary, used for the purpose of accelerating material transfer between an oil phase and an aqueous phase to improve an oxime-formation rate. There are no particular restrictions to a hydrophilic solvent as long as it is inert to hydroxylamine, and alcohols having a boiling point lower than water are suitable. The amount of a hydrophilic solvent is 20% or less, preferably 10% or less to cyclododecanone.

Oil/Aqueous Phase Separation Step

In the subsequent oil/aqueous phase separation step, a reaction mixture after the oxime-forming step is separated into an oil phase and an aqueous phase to obtain the oil phase in which cyclododecanone oxime is dissolved. The oil phase and the aqueous phase can be separated by a commonly used separation method such as standing separation, centrifugation separation and cyclone separation, but in an industrial continuous process, a reaction mixture is tranferred from an oxime-forming reactor to a separator, where the oil and the aqueous phases are separated and drained. Depending on the type of the oxime-forming reactor, the oil phase and the aqueous phase may be drained separately from the reactor.

When oxime formation is conducted using an aqueous solution of hydroxylamine sulfate (hydroxylamine prepared by Rashig method, also called as ammonium sulfite method, where an aqueous solution of ammonium nitrate is reduced by sulfur dioxide in the presence of hydrogen sulfate ions, into hydroxyamide-N,N-disulfate, which is then hydrolyzed to obtain hydroxylamine sulfate) and ammonia water, ammonium sulfate is obtained as a byproduct from the separated aqueous phase. This ammonium sulfate is called as oxime ammonium sulfate, which is purified more easily than ammonium sulfate as a byproduct in the rearrangement step described in "BACKGROUND ART" (called as rearrangement ammonium sulfate) and can be thus sold in the market. When hydroxylamine prepared by HPO method wherein hydroxylamine phosphate is prepared is used, ammonium sulfate is not formed even in the oxime-forming step.

Furthermore, for the purpose of recovering cyclododecanone oxime dissolved in the aqueous phase, for example, a solvent or cyclododecanone co-evaporated with water in the subsequent step is contacted with the aqueous phase in the manner of counter-current flow, to extract cyclododecanone oxime. Alternatively, cyclododecanone oxime, a solvent and/or cyclododecanone dissolved in the aqueous phase may be recovered by an appropriate method such as steam distillation.

Dehydration Step

The next dehydration step removes water dissolved in the oil phase obtained in the oil/aqueous phase separation step. While water present in the oil phase (dissolved water) is in a small amount, the existing water can inactivate a rearrangement catalyst and adversely affects the rearrangement reaction itself, and therefore, it is preferable to conduct dehydration. Dehydration may be conducted by contacting with an adsorbent or dehydrating agent, but it is preferable that dissolved water is (azeotropically) co-evaporated with a solvent or cyclododecanone. Alternatively, blowing an inert gas such as nitrogen is also preferable.

The evaporated water-containing solvent (ester, tertiary alcohol or the like) and/or cyclododecanone is recycled to the oxime-forming step. The residue (a cyclododecanone oxime solution) is transferred to the rearrangement step. Water is removed so that a water concentration in the oil phase becomes 1000 ppm or less, preferably 100 ppm or less.

Rearrangement Step

The dehydrated cyclododecanone oxime solution is transferred to the rearrangement step. In the rearrangement step, laurolactam is formed from cyclododecanone oxime by a rearrangement reaction using the above aromatic-ring containing compound as a rearrangement catalyst.

In addition, a metal salt having Lewis acid properties such as zinc chloride or a Broensted acid such as hydrogen chloride can be added as a co-catalyst to improve a rearrangement reaction rate. In particular, a Lewis acid is preferable because it can improve a rearrangement reaction rate without accelerating hydrolysis of cyclododecanone oxime. Examples of a Lewis acid generally include, but not limited to, zinc chloride, aluminum chloride, antimony pentachloride and tin tetrachloride, particularly preferably zinc chloride which is significantly effective in improving a reaction rate.

The amount of the rearrangement catalyst varies depending on the water content in the cyclododecanone oxime, and is 0.01 mol % to 20 mol %, preferably 0.1 mol % to 5 mol % to cyclododecanone oxime. If the amount of the catalyst is too small, a rearrangement rate is so slow that the reactor must be unfavorably long. In contrast, the excessive amount of the catalyst increases a catalyst cost, and unfavorably increases costs for post-treatment and recycling of the catalyst. The amount of the co-catalyst is 0.1 to 10 molar amount, preferably 0.5 to 5 molar amount to the catalyst. A too small amount of the co-catalyst is less effective in improving a rearrangement rate while an excessive amount of the co-catalyst cannot further improve a rearrangement rate.

A reaction temperature in the rearrangement step is 50° C. to 160° C., preferably 70° C. (or 80° C.) to 110° C. A too low reaction temperature is unfavorable because a reaction rate is reduced, leading to a longer reaction time. At a low temperature, cyclododecanone oxime is less soluble in a solvent for rearrangement or cyclododecanone (in the case an excessive amount of cyclododecanone is used) and the solvent or cyclododecanone to be recovered or recycled is increased. On the other hand, a too high reaction temperature is unfavorable because heat generated in the exothermic rearrangement reaction may cause rapid increase in a temperature to the extent that the reaction cannot be controlled. Furthermore, a too high reaction temperature unfavorably lead to decrease in a rearrangement yield and deterioration in product quality such as coloration problem.

A reaction time of the rearrangement step is 5 min to 10 hours, preferably 20 min to 4 hours. A reaction time varies depending on the type a catalyst, a catalyst concentration and a reaction temperature, but the above reaction conditions are adjusted such that the reaction can be easily controlled and a very large reactor volume is not required.

The conversion of cyclododecanone oxime in the rearrangement step is adjusted by a reaction time. If the conversion of cyclododecanone oxime is 100%, cyclododecanone oxime and laurolactam do not have to be separated and the purification of laurolactam is easy, resulting in an advantage of purification cost reduction. When a cyclododecanone oxime concentration is low, a catalyst used in the present invention tends to react with a trace amount of dissolved water and becomes inactive. Therefore, the rearrangement reaction may be deliberately terminated before the conversion of cyclododecanone oxime reaches 100%, and then some of laurolactam can be separated in the subsequent separation/purification step and then a remaining cyclododecanone oxime, a solvent or cyclododecanone (when an excessive amount of cyclododecanone is used), a catalyst and the remaining laurolactam can be recycled to the first substep in the rearrangement step. When this process is employed, a catalyst turnover is improved and a catalyst cost is reduced.

The conversion may be appropriately selected, in consideration of economic efficiency of the whole process into account. When a catalyst is recycled, a conversion of cyclododecanone oxime is preferably 80% to 95%. If the conversion of cyclododecanone oxime is less than 80%, cyclododecanone oxime recycled is unfavorably increased, leading to a reduced production efficiency per a reactor. On the other hand, if the conversion is over 95%, a rate of the catalyst which is inactivated by water is increased and thus turnover of the catalyst cannot be expected.

The reaction can be conducted under a reduced pressure, an ambient pressure or an increased pressure. Although it is not strongly recommended that the reaction is conducted under an increased pressure, the reaction can be conducted in a closed system, whereby a component eliminated from the catalyst (for example, when the leaving group is halogen, it is hydrogen halide) is prevented from diffusing to the outside of the reaction system. Employing a closed process is preferable because a facility for adsorbing or removing the compound originated from the leaving group can be reduced and the compound originated from the leaving group itself is an acid which can act as a co-catalyst accelerating the rearrangement reaction. The reaction at an ambient pressure is also preferable because a reactor is inexpensive and the reaction can be easily controlled. Furthermore, when an excessive amount of cyclododecanone is used, the rearrangement reaction may be conducted while cyclododecanone is evaporated under a reduced pressure. This utilizes the fact that a solubility of laurolactam in cyclododecanone is higher than cyclododecanone oxime, whereby improving a production efficiency per a unit area of the reactor. This can be also applied to the case where a solvent in which laurolactam is more soluble than cyclododecanone oxime is used.

While a rearrangement reactor can be selected from commonly used reactor such as a batch reactor, preference is given to a tubular reactor and CSTR and CSTR in the light of easy control of a reaction temperature and simple operation.

Separation/Purification Step

"Separation/purification step" is collectively used as the general term for the step where laurolactam contained in the reaction mixture after the rearrangement reaction is separated and purified. The separation/purification step contains, as a part, a step of separating (including removal) laurolactam from the rearrangement catalyst. In the description below, a catalyst separation (or removal) step and a laurolactam crystallization step and so on are the steps for separating laurolactam and the rearrangement catalyst.

Separation and removal of a catalyst can be classified roughly into (1) a method involving inactivation of a catalyst and (2) a method involving recovery of a catalyst.

(1) Method Involving Inactivation of a Catalyst (Involving Conversion of a Catalyst into a Water-Soluble Compound)

A rearrangement catalyst used in the present invention can be quenched by adding water. The leaving group in the catalyst is replaced by hydroxy and the catalyst becomes a water-soluble compound and transfers to an aqueous phase. For example, trichlorotriazine is converted into cyanuric acid, which is soluble in an aqueous phase. For facilitating catalyst removal, an aqueous alkali solution such as ammonia water and an aqueous sodium hydroxide solution can be used without causing any problems. Even when the recovery and recycle of the catalyst is intended, laurolactam may be washed with water or an alkali solution for completely removing the residual catalyst.

(2) Method Involving Recovery of a Catalyst (2-1) When the catalyst has a lower boiling point than the solvent or other agent, the catalyst can be recovered by distillation. For example, trichlorotriazine has a lower boiling point than cyclododecanone (when an excessive amount of cyclododecanone is used), and thus can be recovered by vacuum distillation. The recovered catalyst is preferably recycled to the rearrangement step.

(2-2) A method of separating laurolactam by crystallization while remaining the catalyst in a mother liquid is also suitable. The reaction mixture after the rearrangement reaction is, if necessary, concentrated. Here, it is advantageous that the solvent has a lower boiling point than the catalyst. The solvent recovered by evaporation is preferably recycled to the oxime-forming step. As long as a crystallization temperature is equal to or higher than a melting point of the solvent, the lower crystallization temperature causes the lower concentration of laurolactam remaining in the mother liquid, and thus, the higher a production efficiency is attained. For example, when butyl acetate is used as a solvent, crystallization can be conducted below freezing point. When tert-butanol is used as a solvent, a crystallization temperature is 26° C. or higher. The mother liquid after separating laurolactam contains the catalyst and the solvent, and is preferably recycled to the rearrangement step.

Laurolactam separated from the catalyst as described above is purified as described below. First, when "(1) a method involving inactivation of a catalyst" or "(2-1) a method involving recovery of a catalyst by distillation" is employed for catalyst separation, typically preferably cyclododecanone (when an excessive amount is used) or a solvent is recovered by distillation from the reaction mixture after recovering or separating the catalyst, and laurolactam is further purified by distillation. The recovered cyclododecanone or solvent is preferably recycled to the oxime-forming step. Further purification of laurolactam typically involves distillation operations (including obtaining a product as a distillate, obtaining a product as a still-bottom product, rectification and so forth), which are preferably combined as a multistage procedure. For example, the remianed still residue (still-bottom product) after distillation of cyclododecanone or a solvent as described above can be drained and distilled one or more times to be purified. The distillation is preferably conducted in vacuo.

When laurolactam is separated from a catalyst by "(2-2) a method involving separation of laurolactam by crystallization", crystallized laurolactam can be, if desired, further purified. For further purification of laurolactam, distillation is suitable. Because laurolactam has been purified by crystallization, one distillation operation is adequate to give a high quality product, but for the purpose of improving a distillation yield, multistage distillation can be conducted while a distillation fraction or still-bottom product is recycled.

There are no particular restrictions to the distillation conditions and a distillation apparatus for laurolactam, but for preventing ring opening or polymerization of laurolactam, it is desirable that vacuum distillation is conducted at a vacuum of 10 torr or less such that a bottom temperature is 250° C. or lower, preferably 220° C. or lower.

Figure 1:
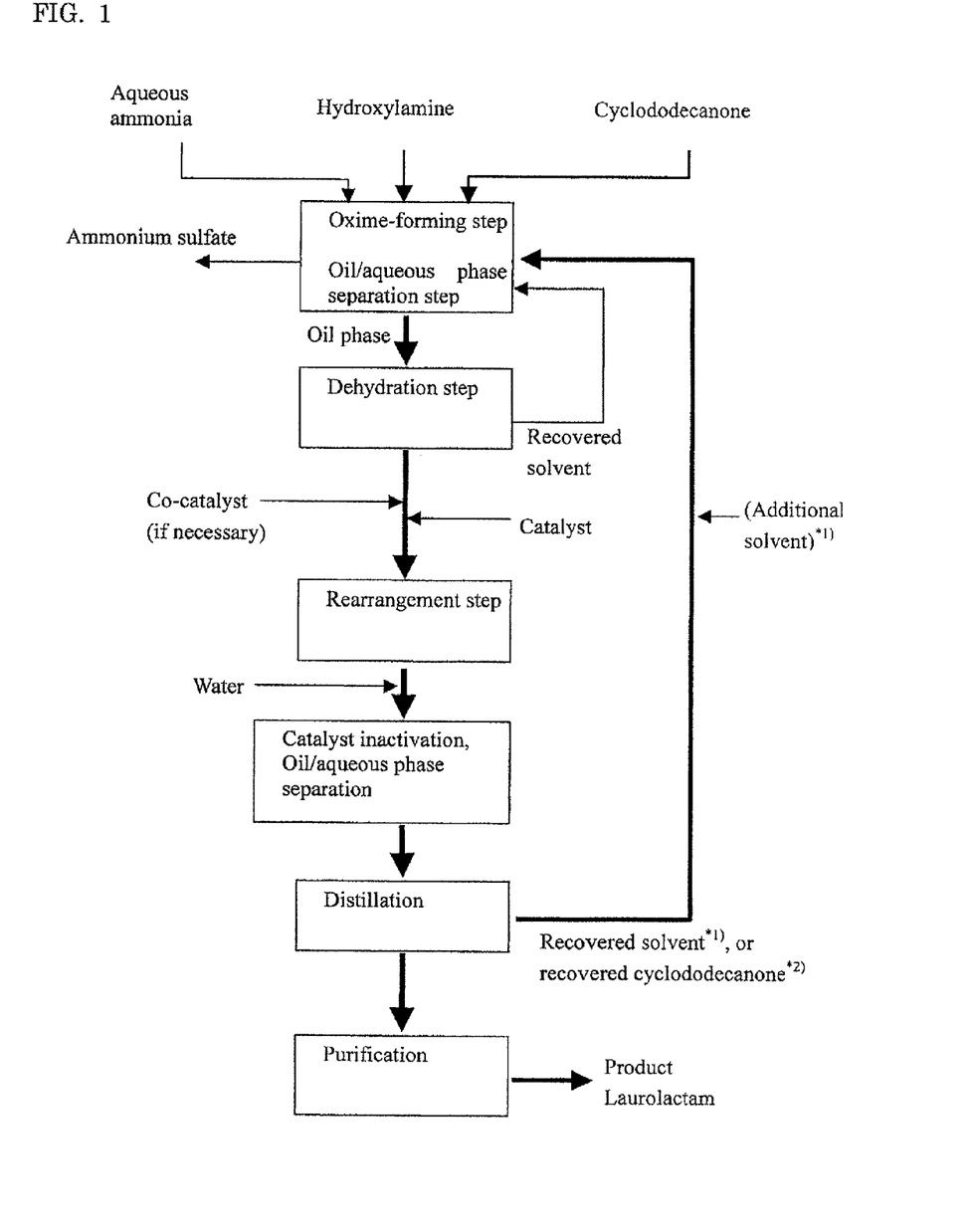
FIG. 1 is a flow chart illustrating an example of the aspect employing "(1) a method involving inactivation of a catalyst". In this figure, *1) "recovered solvent" and "added solvent" are applied to the case where a solvent is used, *2) "recovered cyclododecanone" is applied to the case where the oxime-forming reaction is conducted under the condition of excessive cyclododecanone.

The flow chart in FIG. 1 shows an example of an aspect involving "(1) a method involving inactivation of a catalyst". In this figure, *1) "recovered solvent" and "added solvent" are applied to the case where a solvent is used, *2) "recovered cyclododecanone" is applied to the case where the oxime-forming reaction is conducted under the condition of excessive cyclododecanone.

Figure 2:
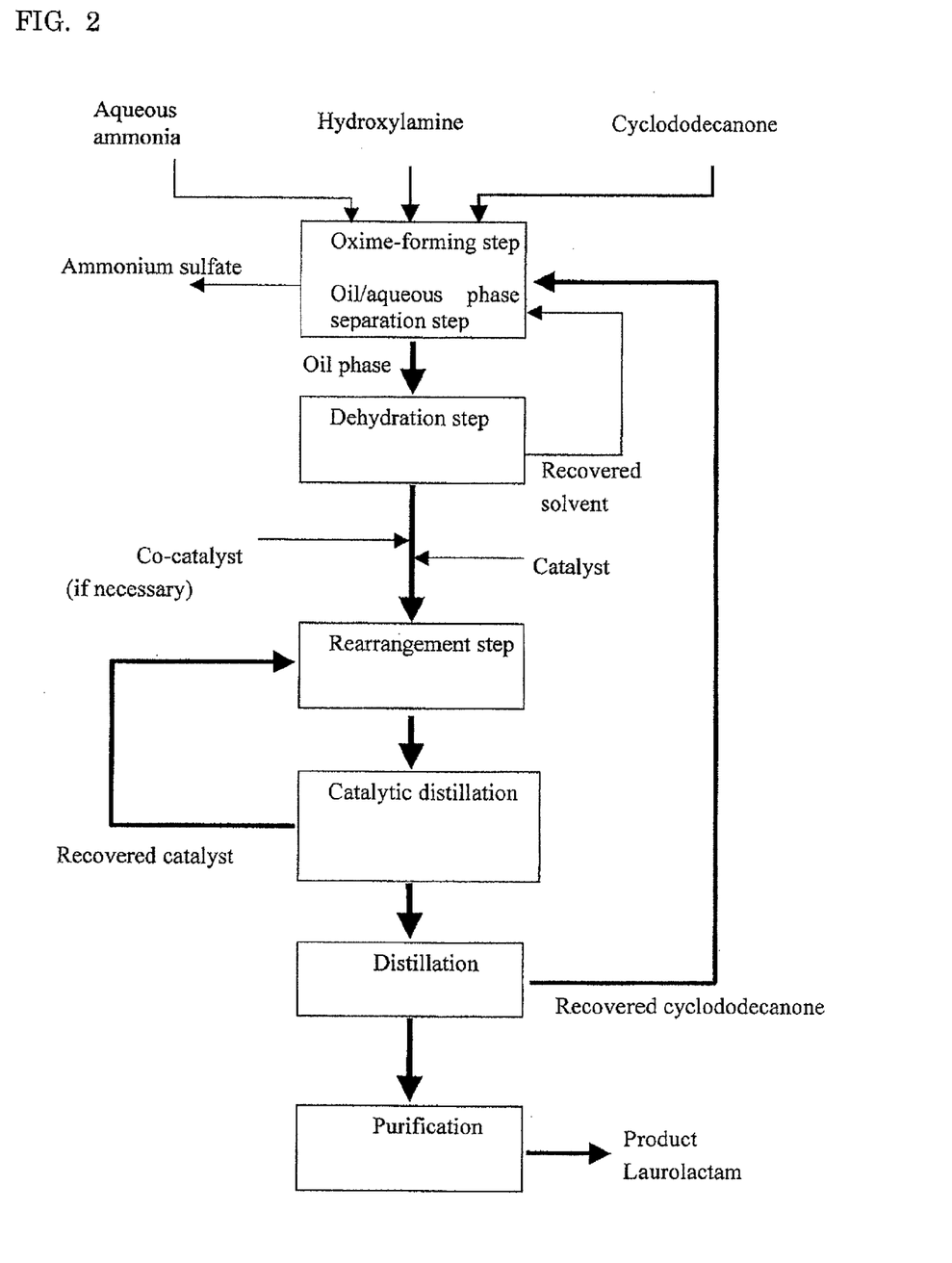
FIG. 2 is a flow chart illustrating an example employing "(2-1) a method involving recovery of a catalyst by distillation". This figure corresponds to the case where the oxime-forming reaction is conducted under the condition of excessive cyclododecanone.

The flow chart in FIG. 2 shows an example employing "(2-1) a method involving recovery of a catalyst by distillation". This figure corresponds to the case where the oxime-forming reaction is conducted under the condition of excessive cyclododecanone.

Figure 3:
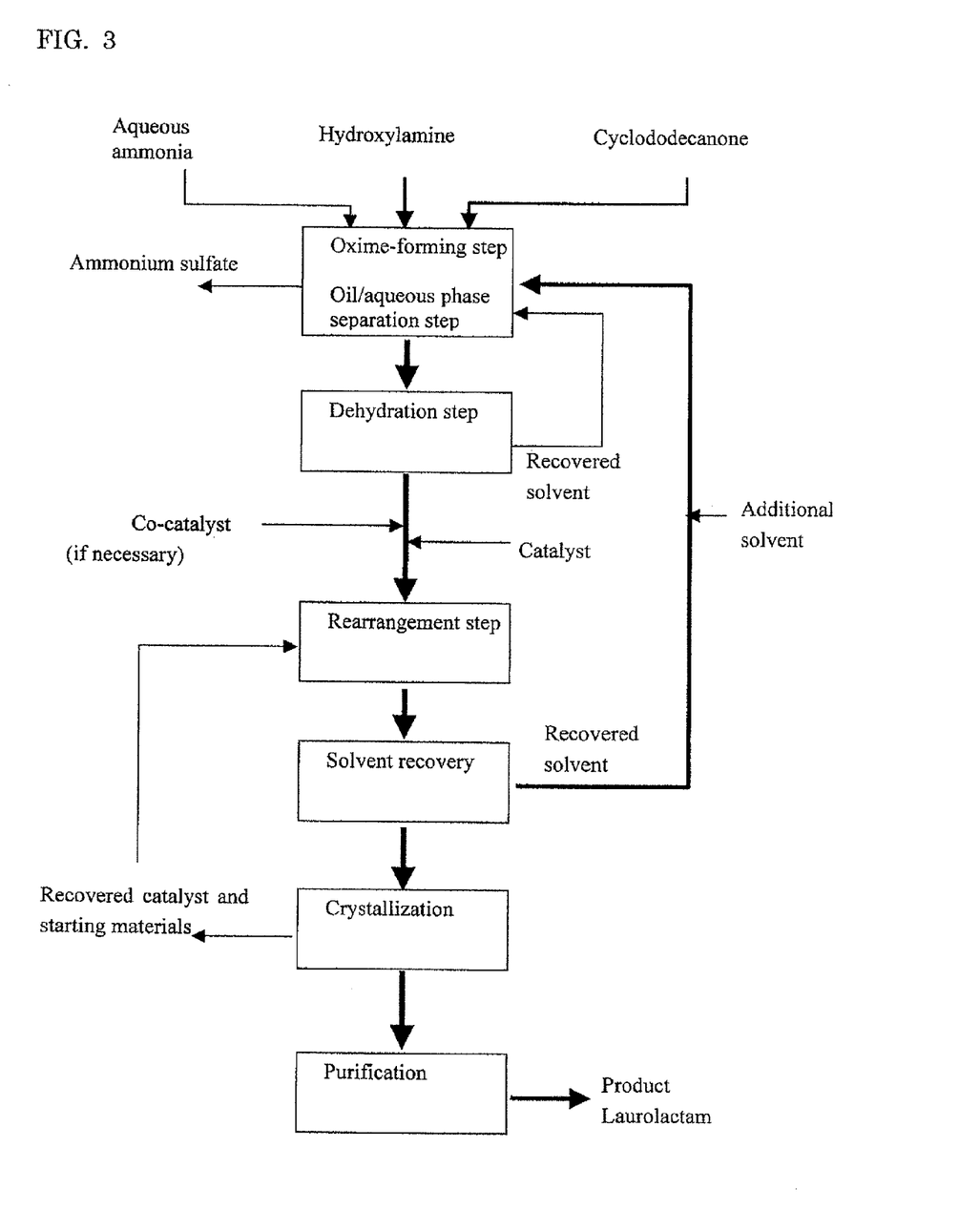
FIG. 3 is a flow chart illustrating an example employing separation of laurolactam and a catalyst by "(2-2) a method involving separation of laurolactam by crystallization".

The flow chart in FIG. 3 shows an example employing separation of laurolactam and a catalyst by "(2-2) a method involving separation of laurolactam by crystallization".

As is clear from the above descriptions, each step in the production process of the present invention may be a combination of two or more substeps, or, if possible, two or more steps may be conducted in the same apparatus or carried out simultaneously. Although the present invention is preferably utilized in a continuous production process, for example, as in an industrial process, some or all steps may be independently conducted.

EXAMPLES

The present invention will be specifically described with reference to Examples. These examples are intended to illustrate embodiments of the present invention, but the present invention is not limited to the examples.

Embodiment A

Embodiment A will illustrate an example where cyclododecanone is used in an excessive amount to hydroxylamine.

Example A-1

Oxime-Forming Step, Oil/Aqueous Phase Separation Step and Dehydration Step

Into a pillow type reactor with a 10 liter liquid phase zone which was internally divided into four chambers each of which was equipped with an agitating blade were fed a combination of cyclododecanone (Tokyo Chemical Industry Co., Ltd.) molten by heating at 80° C. and recovered cyclododecanone described below at 1 kg/h and a 15.2% by weight aqueous solution of hydroxylamine sulfate (Wako Pure Chemical Industries, Ltd.) at 1.2 kg/h, and a reaction was conducted at 97° C. while pH of the aqueous phase was adjusted to pH 6 by adding 25% ammonia water (an average residence time: 4 hours). Without cooling, the effluent from the reactor was separated into an oil phase and an aqueous phase.

To the oil phase thus obtained was bubbled nitrogen gas to dehydrate the oil phase. After dehydration, water concentration in the oil phase was measured by Karl Fischer's method, giving a measured value of 60 ppm. The oil phase was sampled and analyzed by gas chromatography, demonstrating that a production rate of cyclododecanone oxime was 0.428 kg/h and a yield based on the fed hydroxylamine was 97.5%. Cyclododecanone which sublimated during the reaction and nitrogen bubbling was collected by a sublimater, which was then molten and recycled to the oxime-forming reaction reactor.

Rearrangement Step

Into a pillow type reactor with a 1.5 liter liquid phase zone which was internally divided into three chambers each of which was equipped with an agitating blade were fed the solution of cyclododecanone oxime in cyclododecanone obtained in the previous step and a 10% by weight solution of trichlorotriazine dissolved in recovered cyclododecanone described later at 1.03 kg/h and 0.13 kg/h, respectively, and the rearrangement reaction was conducted at 92° C. (average residence time: 1.5 hours). The effluent was sampled and analyzed by gas chromatography, demonstrating that a production rate of laurolactam was 0.411 kg/h and a rearrangement yield was 96.0%.

Separation and Removal of a Catalyst

The reaction mixture obtained in the rearrangement step was introduced into an agitation-vessel type neutralization tank and neutralized by adding a 20% by weight aqueous solution of sodium hydroxide at a rate of 0.1 kg/h, and then oil/aqueous phase separation was conducted in a separation tank (residence time: 10 min).

Recovery of Cyclododecanone and Purification of Laurolactam

Into a continuous vacuum distillator was introduced the separated oil phase and first, water, light byproducts and cyclododecanone were removed. This cyclododecanone containing a trace amount of water was recycled to the oxime-forming step. The still-bottom product was introduced into a second distillator, and cyclododecanone and laurolactam were distilled. The still-bottom product containing laurolactam was recycled to the catalyst removal step. The fraction from the second distillator was fed to a third distilling column, where cyclododecanone and laurolactam were separated. Cyclododecanone distilled from the top of the column was recycled to the rearrangement step and used for dissolving trichlorotriazine. After continuous operation for 8 hours, 92 mol % of laurolactam to the consumed cyclododecanone was obtained.

Embodiment B

Embodiment B will illustrate an example where an ester is used as a solvent.

Example B-1

Oxime-Forming Step and Oil/Aqueous Phase Separation Step

Into a pillow type first reactor for oxime formation with a 30 liter liquid phase zone which was internally divided into four chambers each of which was equipped with an agitating blade were fed a 15% by weight aqueous solution of hydroxylamine sulfate (Wako Pure Chemical Industries, Ltd.) at 3 kg/h and the oil phase from a second reactor for oxime formation. A reaction temperature was set at 80° C., and to each chamber was fed 25% by weight ammonia water at 63 to carry out the oxime-forming reaction. The reaction mixture was separated into phases, and the oil phase containing cyclododecanone oxime and butyl acetate was transferred to the dehydration/solvent-exchange step while the aqueous phase was transferred to the second reactor for oxime formation. The second reactor for oxime formation was a 15 liter pillow type reactor which was internally divided into four chambers, and to the second reactor were fed the above oxime-forming reaction mixture aqueous phase and a 20% by weight solution of cyclododecanone in butyl acetate at 5 kg/h (equimolar amount to hydroxylamine sulfate to the first reactor), and after a reaction temperature was set at 90° C., 25% by weight ammonia water was fed to each chamber at 31 g/h to carry out the oxime-forming reaction.

The reaction mixture obtained was separated into phases and the oil phase was transferred to the first reactor for oxime formation. The aqueous phase was heated to 105° C. and butyl acetate and cyclododecanone oxime dissolved in the aqueous phase were recovered and fed to the second reactor for oxime-formation. The aqueous phase after recovering butyl acetate and cyclododecanone oxime was concentrated and after the precipitated ammonium sulfate was collected, discarded as a waste water.

Dehydration Step

Cyclododecanone oxime obtained in the oil/aqueous phase separation step was transferred to a distillator and dissolved water was removed by co-evaporation with butyl acetate. The distillate was recycled to the oxime-forming step as a solvent for cyclododecanone. The water concentration of the residual liquid was measured by Karl Fischer's method, giving a measured value of 85 ppm. The residual liquid was transferred to the rearrangement step.

Rearrangement Step

Into a pillow type reactor with a 5 liter liquid phase zone which was internally divided into three chambers each of which was equipped with an agitating blade were fed the solution of cyclododecanone oxime in butyl acetate obtained in the previous step and a 3% by weight solution of trichlorotriazine in butyl acetate at 3200 g/h and 1000 g/h, respectively, and the rearrangement reaction was conducted at 80° C. (average residence time 1.0 hour). The effluent was sampled and analyzed by gas chromatography, demonstrating that a production rate of laurolactam was 925 g/h and cyclododecanone oxime remained at 119 g/h. A yield of laurolactam based on cyclododecanone was 85.4% and a yield of cyclododecanone oxime was 11.0% (a conversion of cyclododecanone oxime in the rearrangement step was 89% assuming that a yield in the oxime-forming step was 100%). The rearrangement step was steadily operated for 5 hours.

Crystallization and Separation of Laurolactam

The above rearrangement reaction mixture was introduced into a simple distillator and after evaporating about 12 kg of butyl acetate, the mixture was cooled to 20° C. to precipitate laurolactam. Laurolactam was separated by filtering and rinsed with a small amount of butyl acetate, and its weight after drying was measured, giving a measured value of 3672 g, and its purity was 99.5% as determined by gas chromatography. Cyclododecanone oxime was not detected. The filtrate and the washing were combined and analyzed by gas chromatography, demonstrating that it contained 960 g of laurolactam, 18 g of cyclododecanone and 595 g of cyclododecanone oxime. Yields of crystallized laurolactam, dissolved laurolactam and cyclododecanone oxime based on cyclododecanone were 67.5%, 17.7% and 11.0%, respectively.

Catalyst Recycling Experiment

The filtrate obtained in the step of crystallization and separation of laurolactam was concentrated until the total amount became 5 kg, and fed to the rearrangement step at a rate of 500 g/h. On the other hand, a feeding rate from the dehydration step was kept at 3200 g/h while a feeding rate of the trichlorotriazine solution was reduced to 500 g/h. The effluent was sampled and analyzed by gas chromatography, demonstrating that process-outlet flow rates of laurolactam and cyclododecanone oxime were 1069 g/h and 128 g/h, respectively. A yield of laurolactam produced in the rearrangement step was 85.2% and a conversion of cyclododecanone oxime was 88.8%.

Example B-2

A solution of cyclododecanone oxime in butyl acetate was fed to the rearrangement step at 3200 g/h, while the operation conditions in the oxime-forming step, the oil/aqueous phase separation step and the dehydration step are set as described in Example B-1. The reaction was conducted except that a feeding rate of the 3% by weight solution of trichlorotriazine in butyl acetate was changed to 330 g/h, a 10% by weight solution of zinc chloride in butyl acetate was additionally fed at 75 g/h and a reaction temperature was set at 100° C. The rearrangement reaction tank effluent was sampled and analyzed by GC, demonstrating that cyclododecanone oxime was not detected, a flow rate of laurolactam was 1035 g/h and a yield of laurolactam based on cyclododecanone was 95.6%. After steady operation for 5 hours, to the rearrangement mixture obtained was added 1 kg of water and the mixture was washed with water at 90° C. for 30 min and separated into phases to obtain an oil phase, and after evaporating butyl acetate by an evaporator, laurolactam was distilled and purified under a reduced pressure of 0.2 kPa at 170° C. to give 4100 g of laurolactam. A purity of laurolactam was 99.9%. A yield of laurolactam including laurolactam contained in the initial distillate and the still-bottom product was 5070 g, and a yield of laurolactam based on cyclododecanone was 93.7%.

Embodiment C

Embodiment C will illustrate an example where a solvent is tertiary alcohol.

Example C-1

Oxime-Forming Step and Oil/Aqueous Phase Separation Step

In Example B-1, a solvent was changed from butyl acetate to t-butanol, the same apparatus was used and a reaction temperature in the second reactor for oxime formation was changed from 90° C. to 80° C. Except the above, the same conditions in the oxime-forming step and the oil/aqueous phase separation step described in Example B-1 were employed, and the oxime-forming step and the oil/aqueous phase separation step were conducted.

Dehydration Step

Cyclododecanone oxime obtained in the oil/aqueous phase separation step was transferred to a distillator and dissolved water was evaporated by co-evaporation with t-butanol. The distillate was recycled to the oxime-forming step as a solvent for cyclododecanone. Water concentration of the residue was determined by Karl Fischer's method, giving a measured value of 90 ppm. The residue was fed to the rearrangement step.

Rearrangement Step

The rearrangement step in Example B-1 was repeated. However, a solvent was t-butanol. Analysis of an effluent demonstrated that a production rate of laurolactam was 876 g/h and cyclododecanone oxime remained at 162 g/h. A yield of laurolactam based on cyclododecanone was 80.9% and a yield of cyclododecanone oxime was 15.0% (a conversion of cyclododecanone oxime in the rearrangement step was 85% assuming that a yield in the oxime-forming step was 100 W. The rearrangement step was steadily operated for 5 hours.

Crystallization and Separation of Laurolactam

The above rearrangement reaction mixture was introduced into a simple distillator and after evaporating about 10 kg of t-butanol, the mixture was allowed to be cooled to room temperature to precipitate laurolactam. Laurolactam was separated by filtering and rinsed with a small amount of t-butanol, and its weight after drying was measured, giving a measured value of 2890 g, and its purity was 99.5% as determined by gas chromatography. Cyclododecanone oxime was not detected. The filtrate and the washing were combined and analyzed by gas chromatography, demonstrating that it contained 1480 g of laurolactam, 22 g of cyclododecanone and 800 g of cyclododecanone oxime. Yields of crystallized laurolactam, dissolved laurolactam and cyclododecanone oxime based on cyclododecanone were 53.4%, 27.3% and 14.8%, respectively.

Catalyst Recycling Experiment

A catalyst recycling experiment was conducted as described in Example B-1. The effluent was sampled and analyzed, demonstrating that process-outlet flow rates of laurolactam and cyclododecanone oxime were 1079 g/h and 179 g/h, respectively. A yield of laurolactam produced in the rearrangement step was 80.2% and a conversion of cyclododecanone oxime was 84.6%.

Example C-2

A reaction was conducted as described in Example C-1, except that in the rearrangement step, a feeding rate of a 3% by weight solution of trichlorotriazine in t-butanol was 500 g/h and additionally a 10% by weight of zinc chloride in t-butanol was fed at 75 g/h. A yield of laurolactam to the rearrangement step was 86.2%, and a yield of cyclododecanone oxime was 9.5% (a conversion of cyclododecanone oxime in the rearrangement step was 90.5% assuming that a yield in the oxime-forming step was 100%). A recycling experiment was conducted as described in Example C-1, demonstrating that a conversion of cyclododecanone oxime in the rearrangement step was 90.0% and a yield of laurolactam was 85.5%.

Example C-3

A reaction was conducted as described in Example C-1, except that a reaction solvent was t-amyl alcohol. A yield of laurolactam up to the rearrangement step was 82.0%, and a yield of cyclododecanone oxime was 14.0% (an inversion rate of cyclododecanone oxime in the rearrangement step was 86.0% assuming that a yield in the oxime-forming step was 100%). A recycling experiment was conducted as described in Example C-1, demonstrating that a conversion of cyclododecanone oxime in the rearrangement step was 85.8% and a yield of laurolactam was 81.5%.

Comparative Example C-1

A reaction was conducted as described in Example C-1, except that a reaction solvent was 1-propanol. A yield of laurolactam to the rearrangement step was 9.8%, and a yield of cyclododecanone oxime was 67.4% (a conversion rate of cyclododecanone oxime in the rearrangement step was 32.6% assuming that a yield in the oxime-forming step was 100%), and a large amount of cyclododecanone oxime remained and selectivity of laurolactam in the rearrangement was low.

Comparative Example C-2

A reaction was conducted as described in Example C-1, except that a reaction solvent was cyclohexanol. A yield of laurolactam to the rearrangement step was 26.7%, and a yield of cyclododecanone oxime was 61.4% (a conversion of cyclododecanone oxime in the rearrangement step was 38.6% assuming that a yield in the oxime-forming step was 100%).

There is provided an industrially advantageous and convenient process for producing laurolactam.

What is claimed is:

1. A process for producing laurolactam comprising the steps of:
    (a) reacting cyclododecanone with hydroxylamine in an aqueous solution in the presence of an excess amount of cyclododecanone or a solvent to produce cyclododecanone oxime (hereinafter, referred to as an "oxime-forming step");
    (b) separating the reaction mixture obtained after said oxime-forming step into an oil and an aqueous phases and collecting a solution of cyclododecanone oxime of the oil phase (hereinafter, referred to as an "oil/aqueous phase separation step");
    (c) removing dissolved water from said solution of cyclododecanone oxime which is collected as an oil phase in said oil/aqueous phase separation step (hereinafter, referred to as a "dehydration step");
    (d) producing laurolactam from cyclododecanone oxime by rearrangement reaction using an aromatic-ring containing compound selected from the group consisting of 4-chloro-3,5-dinitrobenzonitrile, picryl chloride, 2-chloro-3,5-dinitropyridine and trichlorotriazine as a rearrangement catalyst (hereinafter, referred to as a "rearrangement step"); and
    (e) separating the produced laurolactam from the reaction mixture after said rearrangement step and purifying the laurolactam (hereinafter, referred to as a "separation/purification step").

2. The process for producing laurolactam according to claim 1, wherein in said dehydration step, a content of residual water in the cyclododecanone oxime solution is reduced to 1000 ppm or less.

3. The process for producing laurolactam according to claim 2, wherein in said dehydration step, a content of residual water in the cyclododecanone oxime solution is reduced to 100 ppm or less.

4. The process for producing laurolactam according to claim 1, wherein in said oxime-forming step, the reaction is conducted in the presence of a solvent selected from carboxylic acid esters and tertiary alcohols.

5. The process for producing laurolactam according to claim 1, wherein in said oxime-forming step, the reaction is conducted in the presence of an excessive amount of cyclododecanone and in said separation/purification step, cyclododecanone is recovered and at least partially recycled to said oxime-forming step.

6. The process for producing laurolactam according to claim 1, wherein in said separation/purification step, water is added to the reaction mixture after the rearrangement step to convert said aromatic-ring containing compound of the rearrangement catalyst into a water-soluble compound and the aqueous layer is separated from the solution containing laurolactam.

7. The process for producing laurolactam according to claim 1, wherein in said separation/purification step, said rearrangement catalyst is recovered from the reaction mixture after the rearrangement step and recycled to said rearrangement step.

8. The process for producing laurolactam according to claim 7, wherein in said separation/purification step, laurolactam is isolated by crystallization from the reaction mixture after the rearrangement step, and said rearrangement catalyst is recovered in the crystallization mother liquid and recycled to said rearrangement step.

9. The process for producing laurolactam according to claim 7, wherein in said rearrangement step, the conversion of cyclododecanone oxime is 95% or less.

* * * * *